(12) United States Patent
Laux et al.

(10) Patent No.: US 11,033,723 B2
(45) Date of Patent: Jun. 15, 2021

(54) TRANSDERMAL THERAPEUTIC SYSTEM COMPRISING AN ELECTRONIC COMPONENT

(71) Applicant: LTS Lohmann Therapie-Systeme AG, Andernach (DE)

(72) Inventors: Wolfgang Laux, Diez (DE); Beatrix Platt, Hausten (DE); Nico Reum, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 16/009,613

(22) Filed: Jun. 15, 2018

(65) Prior Publication Data

US 2018/0289938 A1    Oct. 11, 2018

Related U.S. Application Data

(62) Division of application No. 14/975,478, filed as application No. PCT/EP2014/064166 on Jul. 3, 2014.

(30) Foreign Application Priority Data

Jul. 3, 2013    (EP) .................................... 13174880

(51) Int. Cl.
*A61M 37/00*    (2006.01)
*A61F 13/02*    (2006.01)
(Continued)

(52) U.S. Cl.
CPC ............. *A61M 37/00* (2013.01); *A61F 13/02* (2013.01); *A61F 13/0259* (2013.01);
(Continued)

(58) Field of Classification Search
CPC .......... A61M 37/00; A61M 2205/3592; A61M 2207/00; A61K 9/0097; A61K 45/06;
(Continued)

(56) References Cited

U.S. PATENT DOCUMENTS

| 4,769,028 A | 9/1988 | Hoffman et al. |
| 4,814,168 A | 3/1989 | Sablotsky et al. |

(Continued)

FOREIGN PATENT DOCUMENTS

| CA | 2374930 A1 | 1/2001 |
| CN | 1462185 A | 12/2003 |

(Continued)

OTHER PUBLICATIONS

Office Actions in U.S. Appl. No. 14/443,210, dated Nov. 28, 2016; May 4, 2017; Dec. 11, 2017; Oct. 16, 2018; and Mar. 18, 2019.
(Continued)

*Primary Examiner* — Aradhana Sasan
*Assistant Examiner* — Quanglong N Truong
(74) *Attorney, Agent, or Firm* — ProPat, LLC; Cathy R. Moore

(57) ABSTRACT

Transdermal therapeutic systems are described which have at least one electronic component, as well as methods for producing this type of transdermal therapeutic systems.

15 Claims, 1 Drawing Sheet

(51) Int. Cl.
  *A61K 9/70* (2006.01)
  *A61K 9/00* (2006.01)
  *A61K 45/06* (2006.01)
  *A61F 13/00* (2006.01)
  *A61F 13/84* (2006.01)

(52) U.S. Cl.
  CPC ............ *A61K 9/0097* (2013.01); *A61K 9/703* (2013.01); *A61K 45/06* (2013.01); *A61F 2013/00906* (2013.01); *A61F 2013/0296* (2013.01); *A61F 2013/8479* (2013.01); *A61M 2205/3592* (2013.01); *A61M 2207/00* (2013.01)

(58) Field of Classification Search
  CPC ..... A61K 9/703; A61F 13/02; A61F 13/0259; A61F 2013/8479; A61F 2013/00906; A61F 2013/0296
  See application file for complete search history.

(56) References Cited

U.S. PATENT DOCUMENTS

| | | | |
|---|---|---|---|
| 4,994,267 A | 2/1991 | Sablotsky | |
| 4,994,278 A | 2/1991 | Sablotsky | |
| 5,032,207 A | 7/1991 | Sablotsky et al. | |
| 5,300,291 A | 4/1994 | Sablotsky et al. | |
| 5,405,486 A | 4/1995 | Sablotsky et al. | |
| 5,474,783 A | 12/1995 | Miranda et al. | |
| 5,656,285 A | 8/1997 | Sablotsky et al. | |
| 5,656,286 A | 8/1997 | Miranda et al. | |
| 5,686,099 A | 11/1997 | Sablotsky et al. | |
| 5,719,197 A | 2/1998 | Kanios et al. | |
| 5,958,446 A | 9/1999 | Miranda et al. | |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,884,434 B1 | 4/2005 | Müller et al. | |
| 7,383,083 B2* | 6/2008 | Fischer | A61N 1/044 604/20 |
| 7,847,014 B2* | 12/2010 | Koch | A61K 9/7053 524/563 |
| 8,211,462 B2 | 7/2012 | Breitenbach et al. | |
| 8,246,979 B2 | 8/2012 | Schacht et al. | |
| 9,265,752 B2 | 2/2016 | Wang et al. | |
| 2001/0053383 A1 | 12/2001 | Miranda et al. | |
| 2003/0026830 A1 | 2/2003 | Lauterback et al. | |
| 2003/0060479 A1 | 3/2003 | Brown et al. | |
| 2003/0149394 A1 | 8/2003 | Joshi | |
| 2003/0198662 A1* | 10/2003 | Van Osdol | A61K 9/7061 424/449 |
| 2004/0131897 A1* | 7/2004 | Jenson | H01M 6/40 429/7 |
| 2004/0137045 A1 | 7/2004 | Breitenbach et al. | |
| 2004/0138299 A1 | 7/2004 | Cahill et al. | |
| 2004/0234583 A1 | 11/2004 | Müller | |
| 2005/0019385 A1 | 1/2005 | Houze | |
| 2005/0175678 A1 | 8/2005 | Breitenbach | |
| 2005/0202073 A1 | 9/2005 | Jackson et al. | |
| 2005/0260254 A1 | 11/2005 | Breitenbach et al. | |
| 2006/0263419 A1 | 11/2006 | Wolff | |
| 2009/0048556 A1 | 2/2009 | Durand | |
| 2009/0299304 A1 | 12/2009 | Tang | |
| 2010/0119585 A1 | 5/2010 | Hille et al. | |
| 2010/0286590 A1* | 11/2010 | Durand | A61K 9/0009 604/20 |
| 2010/0311661 A1 | 12/2010 | Kullertz et al. | |
| 2011/0027345 A1 | 2/2011 | Wang et al. | |
| 2011/0104244 A1* | 5/2011 | Hille | A61K 9/7053 424/448 |
| 2014/0046279 A1 | 2/2014 | Leonhard et al. | |
| 2015/0290142 A1 | 10/2015 | Cawello et al. | |

FOREIGN PATENT DOCUMENTS

| | | |
|---|---|---|
| CN | 1606435 A | 4/2005 |
| CN | 1671375 A | 9/2005 |
| CN | 1897935 A | 1/2007 |
| CN | 101146524 A | 3/2008 |
| CN | 101601664 A | 12/2009 |
| CN | 102458397 A | 5/2012 |
| CN | 102770128 A | 11/2012 |
| DE | 10 2012 013 421 A1 | 1/2014 |
| EP | 1 669 063 A1 | 6/2006 |
| EP | 2 177 217 A1 | 4/2010 |
| EP | 2 292 219 A1 | 3/2011 |
| JP | 1998509621 A | 9/1998 |
| JP | 2003-526656 A | 9/2003 |
| JP | 2004-521085 A | 7/2004 |
| JP | 2004-525164 A | 8/2004 |
| JP | 2004-528359 A | 9/2004 |
| JP | 2005-528425 A | 9/2005 |
| JP | 2005-535686 A | 11/2005 |
| JP | 2005-535687 A | 11/2005 |
| JP | 2006-508908 A | 3/2006 |
| JP | 2006515952 A | 6/2006 |
| JP | 2006178807 A | 7/2006 |
| JP | 2007-528392 A | 10/2007 |
| JP | 2009297808 A | 12/2009 |
| JP | 2010-106037 A | 5/2010 |
| JP | 2010158554 A | 7/2010 |
| JP | 2010536434 A | 12/2010 |
| JP | 2011-500647 A | 1/2011 |
| JP | 2011-504902 A | 2/2011 |
| JP | 2011-526592 A | 10/2011 |
| JP | 2012501799 A | 1/2012 |
| JP | 2012-504609 A | 2/2012 |
| JP | 2012-509276 A | 4/2012 |
| JP | 2013-510805 A | 3/2013 |
| JP | 2013-515041 A | 5/2013 |
| WO | 89/10108 A1 | 11/1989 |
| WO | 91/14463 A1 | 10/1991 |
| WO | 92/19451 A1 | 11/1992 |
| WO | 93/00058 A1 | 1/1993 |
| WO | 95/18603 A1 | 7/1995 |
| WO | 99/49852 A1 | 10/1999 |
| WO | WO 00/44437 | 8/2000 |
| WO | 2001/01967 A1 | 1/2001 |
| WO | 2002/015903 A2 | 2/2002 |
| WO | 2002/089777 A1 | 11/2002 |
| WO | 2003/015678 A1 | 2/2003 |
| WO | 2003/092677 A1 | 11/2003 |
| WO | 2004/012721 A2 | 2/2004 |
| WO | 2004/012730 A1 | 2/2004 |
| WO | 2004/050083 A1 | 6/2004 |
| WO | 2005/009424 A1 | 2/2005 |
| WO | 2005/063236 A1 | 7/2005 |
| WO | 2005/063237 A1 | 7/2005 |
| WO | 2005/092331 A1 | 10/2005 |
| WO | WO 2005/119610 | 12/2005 |
| WO | 2008/061639 A1 | 5/2008 |
| WO | 2009/068520 A2 | 6/2009 |
| WO | 2010/042152 A2 | 4/2010 |
| WO | 2011/057714 A3 | 5/2011 |
| WO | 2011/076879 A1 | 6/2011 |
| WO | 2012/071175 A1 | 5/2012 |
| WO | 2012/084969 A1 | 6/2012 |
| WO | 2013/075822 A1 | 5/2013 |
| WO | 2013/075823 A1 | 5/2013 |
| WO | 2013/088254 A1 | 6/2013 |
| WO | 2014/079573 A1 | 5/2014 |
| WO | 2014/195352 A1 | 12/2014 |

OTHER PUBLICATIONS

Office Actions in U.S. Appl. No. 14/975,478, dated Mar. 24, 2017 and Oct. 5, 2017. (parent to U.S. Appl. No. 16/009,613).
Office Action in U.S. Appl. No. 15/312,509, dated Jan. 16, 2018, Jul. 27, 2018 and Jul. 11, 2019.
Office Action in U.S. Appl. No. 15/312,433, dated Jul. 18, 2019.
Office Actions in U.S. Appl. No. 15/312,542, dated Dec. 22, 2017,

(56) References Cited

OTHER PUBLICATIONS

Jul. 17, 2018, Dec. 27, 2018 Jun. 18, 2019 and Nov. 20, 2019.
International Preliminary Report on Patentability, PCT/EP2013/003515, which corresponds to U.S. Appl. No. 14/443,210, filed May 15, 2015.
International Search Report, PCT/EP2013/003515, which corresponds to U.S. Appl. No. 14/443,210, filed May 15, 2015.
Chinese Search Report for the CN Application 201380054953.X, which corresponds to U.S. Appl. No. 14/443,210, filed May 15, 2015.
International Search Report, PCT/EP2015/061099, which corresponds to U.S. Appl. No. 15/312,509, filed Nov. 18, 2016.
International Preliminary Report on Patentability, PCT/EP2014/064166, which corresponds to U.S. Appl. No. 14/975,478, filed Dec. 18, 2015.
Dow Corning: Amine-Compatible Silicone Adhesives, Jul. 28, 2008.
Henkel Corporation, "DURO-TAK and GELVA Transdermal Pressure Sensitive Adhesives," Product Selection Guide, Sep. 2013.
H.F. Hammond in D. Satas "Handbook of Pressure Sensitive Adhesive Techology" (1989) 2nd ed., Chapter 4, Van Nostrand Reinhold, New York, p. 38.
Kandavilli, Sateesh et al., "Polymers in Transdermal Drug Delivery Systems," Pharmaceutical Technology, May 2002, pp. 62-80.
www.ucb.com/investors/Our-equity-story/Neupro(Jan. 6, 2016).
Fachinformation Neupro (Aug. 2011) with English Translation.
"Pressure Sensitive Tack of Adhesives Using an Inverted Probe Machine" ASTM D2979-71 (1982).
K.L. Ulman and R.P. Sweet, "The Correlation of Tape Properties and Rheology" (1998), Information Brochure, Dow Corning Corp., USA.
Yie W. Chien, Transdermal Controlled Systemic Medications 36-45 (Marcel Dekker, Inc. 1987).
Dow Corning Corporation, Material Safety data sheet, Dow Corning 360 Medical Fluid, [(retrieved from on-line website: https://www.b2bcomposites.com/msds/ted/71115.pdf, pp. 1-7, 2010)]. Revision date Sep. 29, 2010.
International Search Report, PCT/EP2015/061112, which corresponds to U.S. Appl. No. 15/312,433, filed Nov. 18, 2016.
JP Application No. 2018-147720 First Office Action, which corresponds to U.S. Appl. No. 16/009,613.
JP Application No. 2016-522618 First Office Action, which corresponds to U.S. Appl. No. 16/009,613.
JP Application No. 2016-522618 Second Office Action, which corresponds to U.S. Appl. No. 16/009,613.
Office Actions in U.S. Appl. No. 15/312,542, dated Jun. 26, 2020.
Office Actions in U.S. Appl. No. 14/443,210, dated Nov. 21, 2019 and Jul. 21, 2020.
Office Actions in U.S. Appl. No. 15/312,433, dated Mar. 23, 2020 and Oct. 21, 2020.
Office Actions in U.S. Appl. No. 15/312,509, dated Apr. 15, 2020 and Dec. 28, 2020.

* cited by examiner

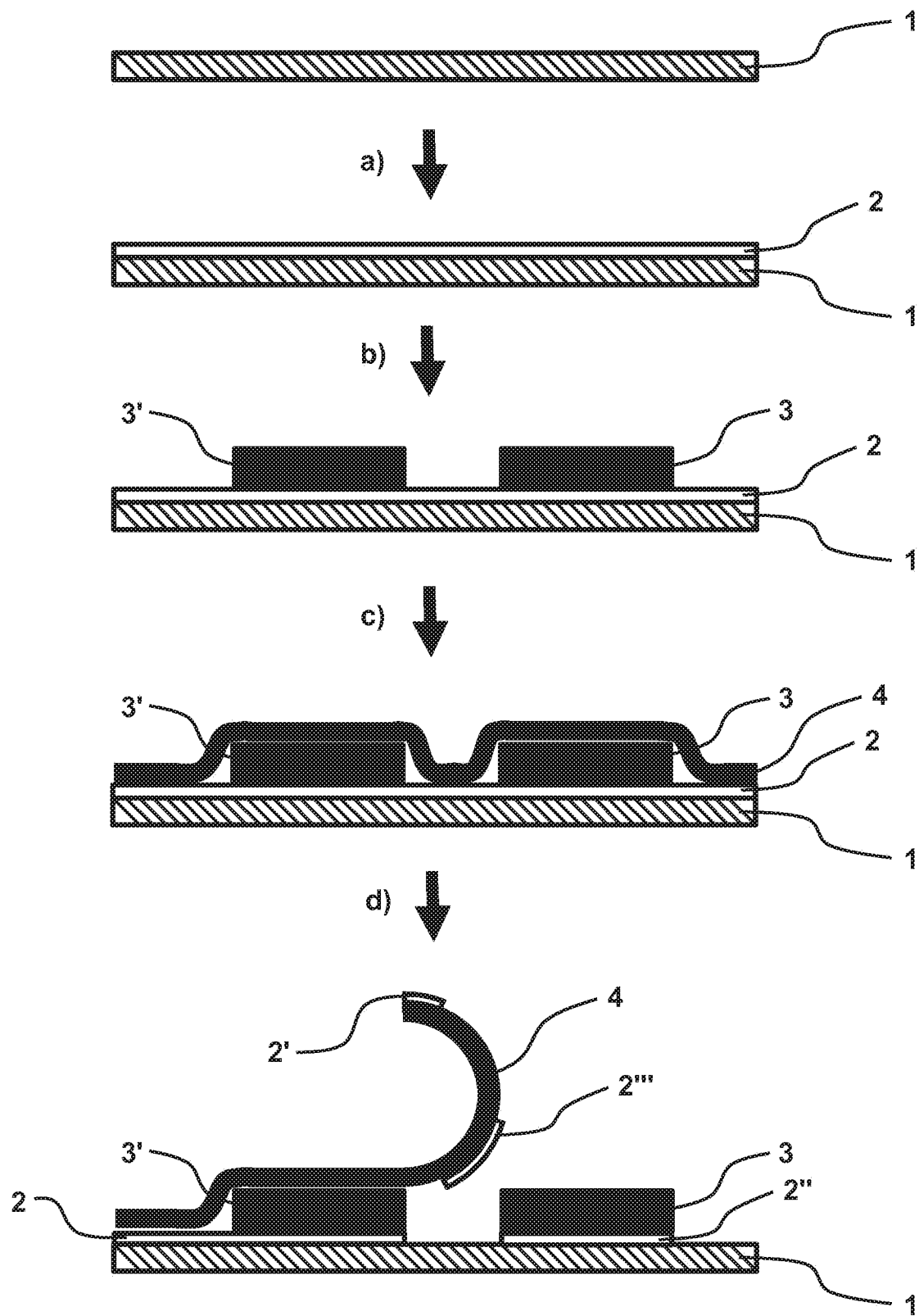

TRANSDERMAL THERAPEUTIC SYSTEM COMPRISING AN ELECTRONIC COMPONENT

The present application is a division of U.S. patent application Ser. No. 14/975,478 filed on Dec. 18, 2015, which claims priority from PCT Patent Application No. PCT/EP2014/064166 filed on Jul. 3, 2014, which claims priority from European Patent Application No. EP 13174880.8 filed on Jul. 3, 3013, the disclosures of which are incorporated herein by reference in their entirety.

FIELD OF THE INVENTION

The invention relates to transdermal therapeutic systems and methods for manufacturing the same. The invention in particular relates to transdermal therapeutic systems which comprise at least one electronic component.

SUMMARY OF THE INVENTION

A transdermal therapeutic system in the following description refers to a device for administering one or more active agents, in particular one or more pharmaceutical active agents, via the intact skin of a mammal. Transdermal therapeutic systems are planar devices which contain at least one active agent and are fastened on the skin or at the skin of a mammal, preferably on or at the skin of a human, so that the active agent contained in the device can be administered to and through the skin of the mammal over a longer period of time at a constant or at least at an approximately constant rate. The attachment of a transdermal therapeutic system at or on the skin of a patient can be effected by means of a bandage or at least an adhesive strip. In particular embodiments the transdermal therapeutic systems, however, are equipped with a pressure-sensitive adhesive. This means that they have a pressure-sensitive surface by means of which they can be adhered to the skin of the mammal and which ensures a long-term contact of the device with the skin of the mammal.

BRIEF DESCRIPTION OF THE DRAWINGS

FIG. 1 is a schematic diagram of some process steps in one embodiment of the method for producing transdermal therapeutic systems which comprise an electronic tag.

DETAILED DESCRIPTION OF EMBODIMENTS

In one embodiment of the transdermal therapeutic systems, the pressure-sensitive surface is formed from a pressure-sensitive polymer matrix which also contains the active agent or at least one of the active agents. In an further and/or alternative embodiment the pressure-sensitive surface is a separate adhesive layer which is applied to at least a portion of the skin-side surface of the transdermal therapeutic system, preferably on the skin-side surface of the active agent reservoir.

The at least one active agent reservoir of a transdermal therapeutic system is either a polymer matrix in which the at least one active agent is included, or a bag-like reservoir which is limited by a shell and contains a substantially liquid active agent preparation. The term "liquid" also encompasses highly fluid, viscous and gel-like preparations. The shell of the bag-like reservoir at least on the side facing to the skin comprises a semi-permeable membrane via which the active agent contained in the reservoir can be discharged and which optionally has a function of controlling the release rate of the active agent. If the at least one active agent is included in a polymer matrix of the transdermal therapeutic system, said polymer matrix has to be considered as an active agent reservoir.

A transdermal therapeutic system includes at least one active agent, preferably at least one pharmaceutical active agent. The at least one pharmaceutical active agent may be any transdermally administrable pharmaceutical active agent. For example, anticholinergics, parasympatholytics, antimycotics, MAO-B inhibitors, serotonin antagonists, alpha2 receptor agonists, photosensitizers, hormones and/or proteins may be used as pharmaceutical active agents. In one embodiment the at least one pharmaceutical active agent is selected from the group of active agents consisting of 5-aminolevulinic acid, buprenorphine, capsaicin, clonidine, fentanyl, granisetron, glyceryl trinitrate, hydromorphone, memantine, oxybutynin, rivastigmine, rotigotine, selegiline and sertaconazole. The at least one pharmaceutical active agent is provided in the form of its free base and/or at least one of its pharmaceutically acceptable salts. The term "pharmaceutically acceptable salt" also includes pharmaceutically acceptable acid addition salts of the active agent. Provided that the at least one active agent is a chiral substance the active agent is present in the transdermal therapeutic system either in the form of a racemate or in form of its pharmaceutically active enantiomer.

In one embodiment transdermal therapeutic systems comprise an active agent impermeable backing layer. In an additional and/or alternative embodiment the transdermal therapeutic systems include a removable protective layer which covers the pressure-sensitive surface of the transdermal therapeutic system prior to its application. The removable protective layer has to be removed from the pressure-sensitive surface prior to the application of the transdermal therapeutic system.

In a first aspect the invention relates to transdermal therapeutic systems which include at least one electronic component.

In a second aspect the invention relates to methods for producing transdermal therapeutic systems which include at least one electronic component.

According to the first aspect the invention relates to transdermal therapeutic systems which comprise at least one electronic component. In one embodiment the at least one electronic component is a passive component, i.e. an electronic component that is not provided with an own power supply.

In an alternative embodiment the at least one electronic component is an active component. Active electronic components in contrast to passive electronic components are provided with an own power supply. In particular embodiments the at least one active electronic component includes at least one voltage source which serves as a power supply of the electronic component. The at least one voltage source may be a solar cell, a capacitor or a galvanic element, for example, a battery or a secondary battery.

According to particular embodiments the at least one electronic component is selected from the group of electronic components consisting of transmitters, receivers, data storages, sensors and measuring instruments.

In a particular embodiment the at least one electronic component is a radio tag. The radio tag may be selected from the group of electronic components consisting of transponders, passive RFID transponders (RFID=radio frequency identification), active RFID transponders, semi-active RFID transponders and semi-passive RFID transponders. Each transponder comprises a microchip, an antenna and a support or housing. Active transponders in addition include the power source. The structure of a RFID transponder in principle includes an antenna, an analog circuit for receiving and transmitting (transceiver) and a digital circuit and a non-volatile memory. The digital circuit in complex models is a small microcontroller.

RFID transponders include an at least write-once memory, which contains their inalterable identity. If rewritable memories are used additional information can be stored during the lifespan.

In particular embodiments the electronic component allows to identify and optionally locate the transdermal therapeutic system which includes the electronic component. The transponder of radio tags is used for storing and/or transferring data. For example, data stored on a transponder can be transferred to a device which is adapted to receive, process, optionally store and display this data. In particular embodiments, the transponder allows storing and/or reading information that may be used for therapy optimization and/or therapy monitoring. Information that can be used for therapy optimization and/or therapy monitoring may be information indicating which agent is contained within the transdermal therapeutic system and in what dosage, when the transdermal therapeutic system has been applied, when the applied transdermal therapeutic system should be removed, when a new transdermal therapeutic system should be applied and if the transdermal therapeutic system is properly attached to the patient or is detached. In a preferred embodiment, the information associated with the time of application, the application duration and/or the intended end time of the application of the transdermal therapeutic system is generated by the activation of the radio tag by means of the contact of the transdermal therapeutic system with the skin.

The electronic component may vary in size and shape. In one embodiment the electronic component is provided in the form of a non-flexible element having a thickness of between approximately 10 µm to approximately 1.5 mm.

In one embodiment the at least one electronic component is applied on the backing layer of the transdermal therapeutic system. This arrangement provides the advantage that prefabricated transdermal therapeutic systems can be provided with an electronic component.

In another embodiment the at least one electronic component is integrated in the transdermal therapeutic system. This means that the at least one electronic component is embedded, for example, in an active agent containing polymer matrix. In an additional and/or alternative embodiment the at least one electronic component is disposed between two matrix layers or between the active agent reservoir and the active agent impermeable backing layer. These embodiments have the advantage that the electronic component becomes an integral part of the transdermal therapeutic system and it is not possible to remove the electronic component without destroying the transdermal therapeutic system.

According to the second aspect the invention relates to a method for producing transdermal therapeutic systems which include at least one electronic component, preferably a radio tag.

In the method according to the second aspect of the invention the electronic components are manufactured separately and the transdermal therapeutic systems are provided with at least one of the prefabricated electronic components either during or after their manufacture. This means in a first embodiment that at least one prefabricated electronic component is mounted on a prefabricated transdermal therapeutic system. In another and/or alternative embodiment at least one prefabricated electronic component is mounted on a not yet fully prefabricated transdermal therapeutic system. In a yet other and/or alternative embodiment at least one prefabricated electronic device is integrated into the transdermal therapeutic system during its manufacture.

In the former embodiment at least one separately produced electronic component is mounted on the backing layer of a prefabricated transdermal therapeutic system or its immediate precursor. To this end, in one variant of this embodiment first a process film is coated on the entire surface with a pressure-sensitive adhesive. In a further step, the electronic components are placed on the adhesive layer and then covered with a cover film. Subsequently, the cover film is peeled off again, wherein the pressure-sensitive adhesive in the areas where no electronic components are placed, is removed with the peeling off of the cover film from the process film. The process film loaded with the electronic components is converted into rolls or in another embodiment subjected to fanfolding. In a further process step the individual electronic components including the adhesive layer adhering to them are transferred onto transdermal therapeutic systems or their immediate precursor by means of a labeling machine.

Prefabricated transdermal therapeutic systems refer to already separated, ready for use transdermal therapeutic systems, i.e. transdermal therapeutic systems that already have their intended surface. Immediate precursors of transdermal therapeutic systems refer to the laminate of the active agent impermeable backing layer, the active agent containing reservoir and the removable protective layer, from which the individual transdermal therapeutic systems are separated by cutting or punching.

The method according to the first embodiment thus comprises:
coating a process film with a pressure-sensitive adhesive,
applying prefabricated electronic components onto the adhesive layer,
covering or lining the adhesive layer and the electronic components applied thereon with a cover film,
removing the cover film,
converting the process film loaded with the electronic components into a roll material or fanfolding the process film loaded with the electronic components,
dispensing the electronic components from the process film loaded with the electronic components by a labeling machine, and
transferring the electronic components onto transdermal therapeutic systems or their immediate precursor.

The process film comprises at least one surface which is dehesive with respect to the adhesive which is to be coated onto the process film. For pressure-sensitive silicone adhesives preferably perfluorinated process films are used. Preferred process films for pressure-sensitive silicone adhesives are, for example, the polyester films commercially available on the filing date of the present disclosure under the trade name Scotchpak™ from 3M Company, St. Paul, Minn. Particularly preferred perfluorinated process films include, for example, the polyester films sold under the trade names Scotchpak™ 1022 and Scotchpak™ 9755 which are coated with fluoropolymer, so that according to the manufacturer's information a "liner release" of <1.0 N/25.4 mm (for Scotchpak™ 1022) or <0.4 N/25.4 mm (for Scotchpak™ 9755) results. Preferred process films which are to be coated with a hydrophilic pressure-sensitive adhesive, for example, a hydrophilic pressure-sensitive acrylate adhesive or a polyisobutylene, in contrast, have a siliconized surface. A process film suitable for hydrophilic pressure-sensitive adhesives is, for example, siliconized paper.

The process film is coated with a pressure-sensitive adhesive. The coating is preferably applied on the entire surface. The coating of the process film with the pressure-sensitive adhesive is carried out such that an adhesive film with a substantially uniform thickness is formed. The thickness of the adhesive film is at least about 10 µm, preferably about 30 µm. The thickness of the adhesive film, however, should not be greater than about 500 µm, and preferably should not exceed a thickness of about 200 µm. An adhesive film of this thickness allows for a safe and precise positioning of the electronic components without causing an undesirably large lateral movement of the electronic components applied onto the process film, as well as a reliable tearing of the adhesive film at the edges of the electronic components when the cover film is peeled off.

The electronic components are preferably the aforementioned radio tags/transponders.

The cover film may be any polymer film, to which the pressure-sensitive adhesive adheres. Suitable cover films consist for example of a polyester such as polyethylene terephthalate. The cover film must be flexible so that it can be pulled over a deflector roll or an edge when it is peeled off. Preferably, the cover film is peeled off while forming an acute angle.

In the method the process film, the adhesive and the cover film are to be selected so that the adhesive adheres more strongly to the cover film than to the process film and the adhesive film tears during the removal of the cover film at the edges of the applied electronic components.

When covering the adhesive layer and the electronic components applied onto the adhesive layer with the cover film the adhesive adheres in those areas at the cover film, in which it is not covered with the electronic components. During the subsequent removal of the cover film the adhesive film adhering to it in the areas where it is not covered by electronic components is peeled off from the process film. Thereby, the adhesive film tears at the edges of the electronic components applied onto the adhesive film, so that the electronic components are not peeled off together therewith but remain on the process film including the areas of the adhesive film covered by them. In this way, a process film loaded with electronic components is obtained which essentially has no free adhesive areas which could affect the further use of the process film then converted into rolls or stacks.

The process film loaded with electronic components is converted into rolls or formed into a stack by fanfolding. Thus the process film loaded with electronic components can be supplied to a labeling machine, by means of which the electronic components coated with the adhesive film can be transferred to transdermal therapeutic systems or their immediate precursor in an automated process step.

The transfer of electronic components coated with an adhesive layer from the process film to transdermal therapeutic systems or their immediate precursor can be implemented manually or by machine. The transfer by machine can be carried out as described above by means of a labeling machine. In a different approach, the individual electronic components can be grasped by a robotic arm, removed from the process foil and placed on the transdermal therapeutic systems or their immediate precursor.

It is basically possible to transfer the electronic components onto already finished, i.e. already separated, transdermal therapeutic systems. In another embodiment, the individual electronic components are transferred onto the immediate precursor of the transdermal therapeutic systems, i.e. onto a laminate, which comprises an active agent impermeable backing layer, at least one active agent containing reservoir and optionally already a detachable protective layer. After transferring the electronic components onto the laminate the individual transdermal therapeutic systems are separated so that they comprise at least one of the electronic components. The separation of the transdermal therapeutic systems is implemented, for example, by punching or cutting out the individual transdermal therapeutic systems from the laminate.

In another implementation of the first embodiment electronic components not provided with adhesive are transferred onto transdermal therapeutic systems or their immediate precursor. In this implementation at least one adhesive area per transdermal therapeutic system is applied onto the backing layer of the transdermal therapeutic system or the immediate precursor by means of screen printing. In this procedure adhesive areas are attached substantially at the positions of the transdermal therapeutic systems or their immediate precursor at which electronic components are to be mounted. The applied adhesive areas have substantially the same surface area and shape as the electronic components to be mounted.

In this implementation the electronic components to be transferred have not to be provided with a pressure-sensitive adhesive, since the adhesive necessary for mounting the electronic components is applied onto the active agent impermeable backing layer. In this embodiment, too, the electronic components can be transferred onto the transdermal therapeutic systems or their immediate precursor manually or by machine. In a variant of the transfer by machine, for example, electronic components stacked in a tube are transferred from below from a dispenser onto transdermal therapeutic systems by means of an arm provided with a vacuum suction cup arm. In another variant the individual electronic components are gripped by a robot arm, preferably gripped laterally and positioned on an adhesive area on the backing layer of a transdermal therapeutic system or its immediate precursor.

In another embodiment at least one electronic component is integrated in a transdermal therapeutic system. This means that the at least one electronic component is disposed between two layers of a multi-layered transdermal therapeutic system, for example, between two active agent containing layers or between the active agent containing reservoir and the active agent impermeable backing layer. Alternatively or additionally at least one electronic component can be embedded in a polymer layer of the transdermal therapeutic system.

In one implementation of this embodiment prefabricated electronic components are not transferred onto the already finished transdermal therapeutic systems, but integrated into transdermal therapeutic systems during their manufacture, for example by applying the electronic components onto the last produced layer of a laminate and subsequently covering them with a further layer. For example, the electronic components are placed directly onto an active agent containing polymer layer, which forms the active agent containing polymer matrix or a part of the active agent containing polymer matrix in the finished transdermal therapeutic system and is covered by another active agent containing polymer layer, an active agent free polymer layer or an active agent impermeable backing layer. If the layer onto which the electronic components are placed is a pressure-sensitive adhesive layer the electronic components need not to be provided with a pressure-sensitive adhesive area. If the layer on which the electronic components are placed, is not a pressure-sensitive adhesive layer, the electronic components can be provided with a pressure-sensitive adhesive area, for example, similar to the former embodiment. In a later process step at least one further layer, for example at least one further active agent containing polymer layer and/or an active agent impermeable backing layer is applied onto the layer provided with electronic components and the individual transdermal therapeutic systems are separated from the resulting laminate such that each individual transdermal therapeutic system comprises at least one electronic component.

This embodiment has the advantage that the at least one electronic component is disposed between an active agent containing polymer matrix and an active agent impermeable backing layer and thus cannot be removed from the transdermal therapeutic system without destroying it.

In a further implementation of this embodiment at least one electronic component is embedded in a polymer matrix. In this case, the electronic component can be cast or pressed into a polymer matrix before a further layer, for example a further matrix layer or the active agent impermeable backing layer is applied onto the polymer matrix.

Hereinafter one embodiment of the method according to the invention is explained in more detail with reference to the figures. It should be noted that the figures are merely illustrative and shall in no way restrict the scope of the invention.

FIG. 1 is a schematic diagram of some process steps in one embodiment of the method for producing transdermal therapeutic systems which comprise an electronic tag.

First, a web of siliconized paper was provided as a process film 1. The process film 1 was coated in a process step a) on an entire surface with an adhesive layer 2. The adhesive was poly[(2-ethylhexyl)acrylate-co-methyl acrylate-co-acrylic acid-co-(2,3-epoxypropyl)methacrylate] (61.5:33:5.5:0.02). This pressure-sensitive acrylate adhesive is commercially available under the trade name DuroTak® 2353 from National Starch, now Henkel. The thickness of the adhesive layer 2 on the process films 1 was 30 µm. Then, radio tags 3, 3' were placed on the adhesive layer 2 (process step b). In a subsequent process step (step c), the radio tags 3, 3' and the remaining free surface of the adhesive layer 2 were covered with a polyethylene terephthalate film as a cover film 4. In the areas where the cover film 4 came into contact with the adhesive layer 2, the cover film 4 adhered to the adhesive layer 2. Then, in step d) the cover film 4 was peeled off again. Thereby the areas 2', 2''' of the adhesive layer 2 which were in contact with the cover film 4 adhered to the cover film 4 and were peeled off together with the cover film 4. The areas 2'' of the adhesive layer 2 covered by the radio tags 3, 3' did not adhere to the cover film 4. When removing the cover film 4 the areas of the adhesive layer 2 adhering to the cover film 4 were separated from the areas of the adhesive layer which were covered by the radio tags 3, 3'. In this way, the radio tags 3, 3' remained on an adhesive layer on the process film 1 which was coextensive with their base surface.

The invention claimed is:

1. A transdermal therapeutic system comprising:
an active agent impermeable backing layer;
at least one active agent containing reservoir;
a removable protective layer; and
at least one electronic component,
wherein the transdermal therapeutic system has a pressure sensitive surface formed from a pressure sensitive polymer matrix which also contains the at least one active agent or wherein the pressure sensitive surface is a separate adhesive layer which is applied to the skin side surface of the transdermal therapeutic system; and
the electronic component consists of a radio tag that either has no power supply or the power supply is a voltage source consisting of a solar cell or capacitor.

2. The transdermal therapeutic system according to claim 1;
wherein the radio tag has no power supply.

3. A transdermal therapeutic system comprising
an active agent impermeable backing layer;
at least one active agent containing reservoir;
a removable protective layer; and
a single electronic component consisting of a radio tag,
wherein the transdermal therapeutic system has a pressure sensitive surface formed from a pressure sensitive polymer matrix which also contains the at least one active agent or wherein the pressure sensitive surface is a separate adhesive layer which is applied to the skin side surface of the transdermal therapeutic system; and
the radio tag has its own power supply.

4. The transdermal therapeutic system according to claim 3;
wherein the radio tag has at least one power source selected from the group consisting of capacitors, solar cells, and galvanic elements.

5. The transdermal therapeutic system according to claim 1;
wherein the at least one electronic component is mounted on the backing layer or is integrated into the transdermal therapeutic system polymer matrix.

6. The transdermal therapeutic system according to claim 1;
wherein the at least one active agent is selected from the group of active agents consisting of anticholinergics, parasympatholytics, antimycotics, MAO-B inhibitors, serotonin antagonists, alpha2-receptor agonist, photosensitizers, hormones and proteins.

7. The transdermal therapeutic system according to claim 6;
wherein the at least one active agent is selected from the group of active agents consisting of 5-aminolevulinic acid, buprenorphine, capsaicin, clonidine, fentanyl, granisetron, glyceryl trinitrate, hydromorphone, memantine, oxybutynin, rivastigmine, rotigotine, selegiline, and sertaconazole.

8. The transdermal therapeutic system according to claim 1;
wherein the transdermal therapeutic system has a pressure sensitive surface formed from a pressure sensitive polymer matrix which also contains the at least one active agent.

9. A transdermal therapeutic system comprising:
an active agent impermeable backing layer;
at least one active agent containing reservoir;
a removable protective layer; and
at least one electronic component,
wherein the transdermal therapeutic system has a pressure sensitive surface formed from a pressure sensitive polymer matrix which also contains the at least one active agent or wherein the pressure sensitive surface is a separate adhesive layer which is applied to the skin side surface of the transdermal therapeutic system, and
said at least one electronic component is mounted to the backing layer via adhesive applied to the backing layer, disposed between two active agent containing polymer layers or an active agent containing polymer layer and the backing layer, or embedded in an active agent containing polymer matrix of the transdermal therapeutic system.

10. The transdermal therapeutic system according to claim 9;
wherein the at least one electronic component comprises at least one radio tag selected from the group consisting of transponders, passive RFID transponders (RFID=radio frequency identification), active RFID transponders, semi-active RFID transponders, and semi-passive RFID transponders.

11. The transdermal therapeutic system according to claim 9;
wherein the electronic component consists of at least one component selected from transmitters, receivers, data storages, sensors and measuring instruments.

12. The transdermal therapeutic system according to claim 9, wherein said adhesive is screen printed.

13. The transdermal therapeutic system according to claim 1, wherein said separate adhesive layer is applied continuously to the skin side surface.

14. A transdermal therapeutic system according to claim 1, wherein the pressure sensitive polymer matrix is formed from polymer consisting of pressure sensitive polymer and the separate adhesive layer formed from polymer consisting of pressure sensitive polymer.

15. A transdermal therapeutic system comprising:
an active agent impermeable backing layer;
at least one active agent containing reservoir;
a removable protective layer; and
at least one electronic component,
wherein the transdermal therapeutic system has a pressure sensitive surface formed from polymer consisting of pressure sensitive polymer that also contains the at least one active agent or wherein the pressure sensitive surface is a separate adhesive layer formed from polymer consisting of pressure sensitive polymer which is applied to the skin side surface of the transdermal therapeutic system,
the transdermal therapeutic system does not comprise a membrane,
and the electronic component is an integral part of the transdermal system and cannot be removed without destroying the transdermal system.

* * * * *